(12) United States Patent
Ropo

(10) Patent No.: US 9,089,720 B2
(45) Date of Patent: Jul. 28, 2015

(54) HAIR GROWTH PROMOTING AGENT CONTAINING 15,15-DIFLUOROPROSTAGLANDIN $F_{2\alpha}$ DERIVATIVE AS ACTIVE INGREDIENT

(75) Inventor: Auli Ropo, Helsinki (FI)

(73) Assignees: SANTEN PHARMACEUTICAL CO., LTD., Osaka (JP); ASAHI GLASS COMPANY, LIMITED, Tokyo (JP)

( * ) Notice: Subject to any disclaimer, the term of this patent is extended or adjusted under 35 U.S.C. 154(b) by 38 days.

(21) Appl. No.: 13/061,690

(22) PCT Filed: Sep. 4, 2009

(86) PCT No.: PCT/JP2009/065462
§ 371 (c)(1),
(2), (4) Date: Mar. 1, 2011

(87) PCT Pub. No.: WO2010/027040
PCT Pub. Date: Mar. 11, 2010

(65) Prior Publication Data
US 2011/0152373 A1 Jun. 23, 2011

(30) Foreign Application Priority Data
Sep. 4, 2008 (JP) ................................. 2008-227066

(51) Int. Cl.
*A61Q 7/00* (2006.01)
*A61K 31/5575* (2006.01)
*A61K 8/69* (2006.01)

(52) U.S. Cl.
CPC ... *A61Q 7/00* (2013.01); *A61K 8/69* (2013.01); *A61K 31/5575* (2013.01)

(58) Field of Classification Search
None
See application file for complete search history.

(56) References Cited

U.S. PATENT DOCUMENTS

| | | | |
|---|---|---|---|
| 5,886,035 A * | 3/1999 | Shirasawa et al. | 514/530 |
| 6,262,105 B1 * | 7/2001 | Johnstone | 514/430 |
| 2002/0172693 A1 | 11/2002 | DeLong et al. | |
| 2004/0115234 A1 * | 6/2004 | Gewirtz | 424/401 |
| 2007/0254920 A1 | 11/2007 | deLong et al. | |
| 2008/0107738 A1 * | 5/2008 | Philips et al. | 424/489 |
| 2009/0186885 A1 | 7/2009 | Johnson et al. | |

FOREIGN PATENT DOCUMENTS

| | | |
|---|---|---|
| EP | 0 850 926 A2 | 7/1998 |
| EP | 1 864 666 A1 | 12/2007 |
| JP | 10-259179 A | 9/1998 |
| JP | 2002-293771 A | 10/2002 |
| JP | 2003-321442 A | 11/2003 |
| JP | 2004-2462 A | 1/2004 |
| WO | WO 98/33497 A1 | 8/1998 |
| WO | WO 01/74315 A2 | 10/2001 |

OTHER PUBLICATIONS

Hollo, The side effects of the prostaglandin analogues, Expert Opin. Drug Saf. (2007) 6(1):45-52.*
Li Ni et al, Travoprost compared with other prostaglandin analogues or timolol in patients with open-angle glaucoma or ocular hypertension: meta-analysis of randomized controlled trials, Clinical & Experimental Ophthalmology, 2006.11, vol. 34, No. 8, pp. 755-764.
Egorov Evgeny et al, Adjunctive use of tafluprost with timolol provides additive effects for reduction of intraocular pressure in patients with glaucoma, European Journal of Ophthalmology, 2009, vol. 19, No. 2, pp. 214-222 (Mar.-Apr. 2009).
Tapurosu (Toroku Shohyo) Tengan'eki 0.0015% Tenpu Bunsho, 2008. 12, pp. 1-4 (for translation see Cite No. 4).
Ophthalmic Solution for the Treatment of Glaucoma/Ocular Hypertention, Tapros ophthalmic solution 0.0015% (Tafluprost); package insert; Oct. 2008 (4 pages).

* cited by examiner

*Primary Examiner* — Brian-Yong Kwon
*Assistant Examiner* — Jennifer A Berrios
(74) *Attorney, Agent, or Firm* — Holtz, Holtz, Goodman & Chick PC

(57) ABSTRACT

The present invention provides a new pharmaceutical application of a 15,15-difluoroprostaglandin $F_{2\alpha}$ derivative. As a result of intensive studies in order to find a new pharmaceutical application of a 15,15-difluoroprostaglandin $F_{2\alpha}$ derivative, it was found that, in a European Phase III clinical trial for tafluprost, one of the 15,15-difluoroprostaglandin $F_{2\alpha}$ derivatives, with patients with open-angle glaucoma or ocular hypertension, tafluprost has actions of growing eyelashes, making eyelashes thicker, and changing the color thereof, that is, has an effect of promoting the growth of hair (eyelashes). Therefore, a 15,15-difluoroprostaglandin $F_{2\alpha}$ derivative is useful as a hair growth promoting agent, and is expected to be useful as an active ingredient of a preventive or therapeutic agent for a disease associated with hair such as alopecia and a hair care product or a hair cosmetic product for regrowing hair, growing hair, increasing hair density, nourishing hair, or the like.

4 Claims, No Drawings

HAIR GROWTH PROMOTING AGENT CONTAINING 15,15-DIFLUOROPROSTAGLANDIN $F_{2\alpha}$ DERIVATIVE AS ACTIVE INGREDIENT

TECHNICAL FIELD

The present invention relates to a hair growth promoting agent containing a 15,15-difluoroprostaglandin $F_{2\alpha}$ derivative as an active ingredient. The hair growth promoting agent is expected to be useful as an active ingredient of a preventive or therapeutic agent for a disease associated with hair such as alopecia and a hair care product or a hair cosmetic product for regrowing hair, growing hair, increasing hair density, nourishing hair, or the like.

BACKGROUND ART

It is said that a human generally has from about 100,000 to 150,000 hairs. The hair repeats a cycle including anagen, catagen, and telogen phases, and then falling out with a period of 3 to 6 years. As a result, about 50 to 200 hairs fall out on average each day.

In general, alopecia refers to a condition in which the ratio of hairs in the anagen phase in this cycle is decreased and hairs in the catagen or telogen phase are increased.

It is considered that alopecia is caused by one and/or a plurality of factors of a decrease in the function of the hair follicles due to androgen, a decrease in the function of metabolism of the hair follicles and roots, a decrease in the physiological function of the scalp, blood circulation disorder in the scalp, poor nutrition, stress, side effects of drugs, aging, heredity, and the like. However, a definite cause has not been identified yet.

In the conventional prevention or treatment of alopecia, supply of nutrients (such as amino acids and vitamins) to the hair and hair follicles, blood circulation promotion by local stimulation, enhancement of the function of the hair follicles, a blood circulation promoting agent, an anti-androgen agent, an anti-seborrheic agent, a keratolytic agent, a disinfectant and antiinflammatory agent, and the like are used alone or in combination of two or more of them.

Further, minoxidil, finasteride, or the like is considered to be effective in the prevention or treatment of alopecia and is often used recently.

In addition, it has been reported that latanoprost which is a representative prostaglandin $F_{2\alpha}$ derivative and the like also have an action of regrowing hair or an action of growing hair (WO 2001/074315 and WO 98/33497).

On the other hand, European Patent Application Publication No. 850926 and JP-A-2004-002462 disclose a 15,15-difluoroprostaglandin $F_{2\alpha}$ derivative, JP-A-10-259179 discloses a fluorine-containing prostaglandin $F_{2\alpha}$ derivative having a multisubstituted aryloxy group, JP-A-2002-293771 discloses an ether-type difluoroprostaglandin $F_{2\alpha}$ derivative, JP-A-2003-321442 discloses a difluoroprostaglandin $F_{2\alpha}$ amide derivative, and JP-A-2006-306862 discloses the action of protecting retinal neurons of a 15,15-difluoroprostaglandin $F_{2\alpha}$ derivative.

However, the action of promoting the growth of hair of a 15,15-difluoroprostaglandin $F_{2\alpha}$ derivative has not been known at all.

SUMMARY OF THE INVENTION

Problems that the Invention is to Solve

It is a very interesting subject to find a new pharmaceutical application of a 15,15-difluoroprostaglandin $F_{2\alpha}$ derivative.

Means for Solving the Problems

The present inventor made intensive studies in order to find a new pharmaceutical application of a 15,15-difluoroprostaglandin $F_{2\alpha}$ derivative. As a result, the inventor found that in a European Phase III clinical trial for tafluprost, one of the 15,15-difluoroprostaglandin $F_{2\alpha}$ derivatives, with patients with open-angle glaucoma or ocular hypertension, tafluprost has actions of growing eyelashes, making eyelashes thicker, and changing the color thereof, that is, has an effect of promoting the growth of hair (eyelashes), and thus the present invention was completed.

That is, the present invention relates to a hair growth promoting agent containing at least one 15,15-difluoroprostaglandin $F_{2\alpha}$ derivative as an active ingredient. The hair growth promoting agent is expected to be useful as an active ingredient of a preventive or therapeutic agent for a disease associated with hair such as alopecia and a hair care product or a hair cosmetic product for regrowing hair, growing hair, increasing hair density, nourishing hair, or the like.

In the present invention, the "15,15-difluoroprostaglandin $F_{2\alpha}$ derivative" means a prostaglandin $F_{2\alpha}$-related compound derived from a prostanoic acid skeleton, and has two fluorine atoms at the 15-position of the prostanoic acid skeleton.

Specific examples thereof include a 15,15-difluoroprostaglandin $F_{2\alpha}$ derivative or a salt thereof disclosed in European Patent Application Publication No. 850926, JP-A-2004-002462, JP-A-10-259179, JP-A-2002-293771, JP-A-2003-321442, or the like.

Preferred examples thereof include a 15,15-difluoroprostaglandin $F_{2\alpha}$ derivative which is a compound represented by the following general formula (1) or a salt thereof.

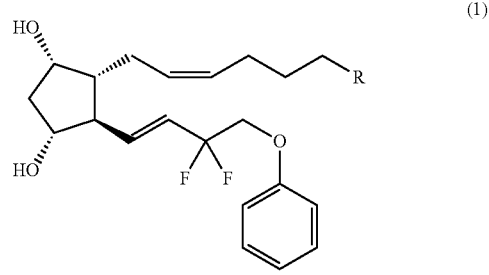

(1)

In the formula, R represents a hydroxyalkyl group, a formyl group, a carboxy group, an alkoxycarbonyl group, an aryloxycarbonyl group, an aminocarbonyl group, an alkylaminocarbonyl group, or an arylaminocarbonyl group, and when R is an aryloxycarbonyl group or an arylaminocarbonyl group, the aryl moiety thereof may have a substituent; and the benzene ring in the formula may have one to three atoms or groups selected from a halogen atom and a trifluoromethyl group as substituents. Hereinafter, the same shall apply.

The respective groups and terms defined in this specification will be shown below.

The "halogen" refers to fluorine, chlorine, bromine or iodine.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, and isopentyl.

The "alkoxy" refers to straight-chain or branched alkoxy having 1 to 6 carbon atoms. Specific examples thereof include methoxy, ethoxy, n-propoxy, n-butoxy, n-pentyloxy, n-hexyloxy, isopropoxy, isobutoxy, sec-butoxy, tert-butoxy, and isopentyloxy.

The "aryl" refers to monocyclic aromatic hydrocarbon, or bicyclic or tricyclic condensed polycyclic aromatic hydrocarbon having 6 to 14 carbon atoms. Specific examples thereof include phenyl, naphthyl, anthryl, and phenanthryl.

The "aryloxy" refers to monocyclic aromatic hydrocarbonoxy, or bicyclic or tricyclic condensed polycyclic aromatic hydrocarbonoxy having 6 to 14 carbon atoms. Specific examples thereof include phenoxy, naphthyloxy, anthryloxy, and phenanthryloxy.

The "alkylamino" refers to monoalkylamino or dialkylamino having 1 to 12 carbon atoms. Specific examples thereof include methylamino, ethylamino, dimethylamino, and dihexylamino.

The "arylamino" refers to monoarylamino or diarylamino having 6 to 28 carbon atoms. Specific examples thereof include phenylamino, naphthylamino, methylphenylamino, ethylphenylamino, diphenylamino, and dianthrylamino.

In the case where R is an "aryloxycarbonyl group" or an "arylaminocarbonyl group", the aryl moiety thereof may have a substituent. The preferred substituent is an atom or a group selected from the group consisting of a halogen atom, an alkyl group, a halogenated alkyl group, and an alkoxy group, and the number of the substituents is preferably from 1 to 3.

The phenyl group in the w-chain of the 15,15-difluoroprostaglandin $F_{2\alpha}$ derivative may have one to three halogen atoms or trifluoromethyl groups. The preferred halogen atom is a fluorine atom or a chlorine atom, and a chlorine atom is particularly preferred.

More preferred examples of the 15,15-difluoroprostaglandin $F_{2\alpha}$ derivative include a 15,15-difluoroprostaglandin $F_{2\alpha}$ derivative wherein, in the above-mentioned general formula (1), R represents a carboxy group or a base thereof or an alkoxycarbonyl group.

Particularly preferred examples of the 15,15-difluoroprostaglandin $F_{2\alpha}$ derivative include a 15,15-difluoroprostaglandin $F_{2\alpha}$ derivative wherein, in the above-mentioned general formula (1), R represents a carboxy group or a base thereof or an isopropyloxycarbonyl group.

These 15,15-difluoroprostaglandin $F_{2\alpha}$ derivatives can be in the form of a salt with an inorganic acid such as hydrochloric acid, hydrobromic acid, hydroiodic acid, nitric acid, sulfuric acid, or phosphoric acid; an organic acid such as acetic acid, fumalic acid, maleic acid, succinic acid, or citric acid; an alkali metal such as lithium, sodium, or potassium; an alkaline earth metal such as calcium or magnesium; ammonia; or the like. These salts are also included in the present invention.

In the present invention, the "hair" is not particularly limited as long as it is human or animal body hair, and head hair, eyebrows, eyelashes, and beards are more preferred, and eyelashes are particularly preferred.

In the present invention, the "hair growth promoting agent" can be used as an agent for promoting the growth of hair, for example, for regrowing hair, growing hair, increasing hair density, nourishing hair, or the like, and more specifically, it can be used as a preventive or therapeutic agent for a disease associated with hair such as alopecia and a hair care product or a hair cosmetic product such as a hair regrowth agent, a hair growth agent, a hair density increasing agent, or a hair nourishing agent.

Further, the use thereof for animals for commercial fur harvesting purposes or the like is also included in the scope of the present invention.

In the case where the hair growth promoting agent of the present invention is used as a pharmaceutical, it can be administered orally or parenterally. Examples of the dosage form thereof include an ointment, an aerosol, an eye drop, an injection, a tablet, a capsule, a granule, and a powder, and particularly preferred is an ointment. Such a preparation can be prepared by any of widely used techniques, for example, a technique disclosed in European Patent Application Publication No. 850926, JP-A-2004-002462, JP-A-10-259179, JP-A-2002-293771, JP-A-2003-321442, JP-A-2006-306862, or the like.

For example, the ointment can be prepared using a widely used base such as white petrolatum or liquid paraffin according to need.

The eye drop can be prepared using a tonisity agent such as sodium chloride or concentrated glycerin; a buffer such as sodium phosphate or sodium acetate; a surfactant such as polyoxyethylene sorbitan monooleate, polyoxyl 40 stearate, or polyoxyethylene hydrogenated castor oil; a stabilizer such as sodium citrate or sodium edentate; a preservative such as benzalkonium chloride or paraben according to need. Any pH value of the eye drop is permitted as long as it falls within the range that is acceptable in an ophthalmic preparation. A preferred pH is in the range of from 4 to 8.

Further, an oral preparation such as a tablet, a capsule, a granule, or a powder can be prepared using an extender such as lactose, crystalline cellulose, starch, or a vegetable oil; a lubricant such as magnesium stearate or talc; a binder such as hydroxypropyl cellulose or polyvinylpyrrolidone; a disintegrant such as carboxymethyl cellulose calcium or low-substituted hydroxypropylmethyl cellulose; a coating agent such as hydroxypropylmethyl cellulose, macrogol, or a silicone resin; a film forming agent such as gelatin film, or the like according to need.

The dose of the 15,15-difluoroprostaglandin $F_{2\alpha}$ derivative can be appropriately selected depending on the symptoms, age, dosage form, and the like. An ointment may be applied once to several times a day at a concentration of from 0.000001 to 3% (w/v), preferably from 0.0001 to 1% (w/v). An oral preparation may be administered once or divided into several times a day at a daily dose of generally from 0.001 to 5,000 mg, preferably from 0.1 to 1,000 mg.

In the case where the hair growth promoting agent of the present invention is used as an active ingredient of a hair care product or a hair cosmetic product, the hair growth promoting agent is added, using a technique widely used to a lotion, a hair tonic, a hair lotion, a hair cream, a hair shampoo, a hair conditioner, a mascara, an eye shadow, an eye liner, or the like, to form a preparation.

Additional components for the hair care product or the hair cosmetic product vary depending on the dosage form thereof. The following components are used according to need and a preparation can be formed:
oil components including hydrocarbons such as liquid paraffin, heavy liquid isoparaffin, solid paraffin, α-olefin oligomer, squalane, petrolatum, polyisobutylene, polybutene, montan wax, ceresin wax, microcrystalline wax, polyethylene wax, and Fisher-Tropsch wax; fats and oils such as olive oil, castor oil, jojoba oil, mink oil, and macademia nut oil; waxes such as beeswax, candelilla wax, spermaceti wax, candelilla wax, carnauba wax, and Japan wax; esters such as cetyl 2-ethylhexanoate, cetyl isooctanoate, isopropyl myristate, isopropyl palmitate, octyldodecyl myristate, polyglyceryl diisostearate, polyglyceryl triisostearate, diglyceryl triisostearate, polyglyceryl tetraisostearate, diglyceryl tetraisostearate, trioctanoin, diisostearyl malate, neopentyl glycol dioctanoate, propylene glycol didecanoate, cholesteryl fatty acid ester, isopropyl myristate, glyceryl monostearate, glycerin fatty acid ester eicosadioate condensate, dextrin palmitate, dextrin myristate, and dextrin fatty acid ester; fatty acids such as stearic acid, lauric acid, myristic acid, behenic acid, isostearic acid, and oleic acid; higher alcohols such as stearyl alcohol, cetyl alcohol, lauryl alcohol, oleyl alcohol, isostearyl alcohol, behenyl alcohol, stearyl alcohol, octyldodecanol, and isohexadecyl alcohol; silicones such as low-polymerized dimethylpolysiloxane, high-polymerized dimethylpolysiloxane, methylphenylpolysiloxane, decamethylcyclopentasiloxane, octamethylcyclotetrasiloxane, polyether-modified polysiloxane, polyoxyalkylene/alkylmethylpolysiloxane/methylpolysiloxane copolymers, and alkoxy-modified polysiloxane; fluorinated oils such as perfluorodecane, perfluorooctane, and perfluoropolyether; N-acylglutamic acid such as stearoyl glutamic acid; amino acid ester oils such as di(cholesteryl or phytosterol/behenyl/octyldodecyl) N-lauroyl-L-glutamate; lanolin derivatives such as lanolin, liquid lanolin, lanolin acetate, liquid lanolin acetate, isopropyl lanolin fatty acid, and lanolin alcohol; and the like;

aqueous components including lower alcohols such as ethyl alcohol and butyl alcohol; glycols such as propylene glycol, 1,3-butylene glycol, dipropylene glycol, and polyethylene glycol; glycerols such as glycerin, diglycerin, and polyglycerin; plant extracts such as aloe vera, witch hazel, hammamelis, cucumber, tomato, apple, lemon, lavender, and rose; and the like;

polymer emulsions including alkyl acrylate copolymer emulsions, alkyl methacrylate polymer emulsions, alkyl acrylate copolymer emulsions, alkyl methacrylate copolymer emulsions, acrylic acid/alkyl acrylate copolymer emulsions, methacrylic acid/alkyl methacrylate copolymer emulsions, alkyl acrylate/styrene copolymer emulsions, alkyl methacrylate/styrene copolymer emulsions, vinyl acetate polymer emulsions, polyvinyl acetate emulsions, vinyl acetate-containing copolymer emulsions, vinylpyrrolidone/styrene copolymer emulsions, silicone-containing copolymer emulsions, and the like; anionic surfactants including soap base materials; fatty acid soaps such as sodium laurate and sodium palmitate; higher alkyl sulfate ester salts such as sodium lauryl sulfate and potassium lauryl sulfate; alkyl ether sulfate ester salts such as triethanolamine polyoxyethylene (POE) lauryl sulfate and sodium POE lauryl sulfate; N-acyl sarcosinates such as sodium lauroyl sarcosinate; higher fatty acid amide sulfonates such as sodium N-myristoyl-N-methyl taurate, sodium coconut oil fatty acid methyl taurate, and sodium lauryl methyl taurate; phosphate ester salts such as sodium POE oleylether phosphate and POE stearylether phosphate; sulfosuccinates such as di-2-ethylhexyl sodium sulfosuccinate, sodium monolauroyl monoethanolamide polyoxyethylene sulfosuccinate, and sodium lauryl polypropylene glycol sulfosuccinate; alkyl benzene sulfonates such as sodium linear dodecyl benzene sulfonate, triethanolamine linear dodecyl benzene sulfonate, and linear dodecyl benzene sulfonate; N-acyl glutamates such as monosodium N-lauroyl glutamate, disodium N-stearoyl glutamate, and monosodium N-myristoyl-L-glutamate; higher fatty acid ester sulfate ester salts such as sodium hydrogenated coconut oil fatty acid glyceryl sulfate; sulfated oils such as Turkey red oil; POE alkyl ether carboxylates; POE alkyl allyl ether carboxylates; α-olefin sulfonates; higher fatty acid ester sulfonates; secondary alcohol sulfate ester salts; higher fatty acid alkylolamide sulfate ester salts; sodium lauroyl monoethanolamide succinate; ditriethanolamine N-palmitoylaspartate; casein sodium; and the like; cationic surfactants including alkyl trimethyl ammonium salts such as stearyl trimethyl ammonium chloride and lauryl trimethyl ammonium chloride; dialkyl dimethyl ammonium salts such as distearyl dimethyl ammonium chloride; alkyl pyridinium salts such as poly(N,N'-dimethyl-3,5-methylenepiperidinium)chloride and cetylpyridinium chloride; alkyl quaternary ammonium salts; alkyl dimethyl benzyl ammonium salts; alkyl isoquinolinium salts; dialkyl morpholinium salts; POE alkylamines; alkylamine salts; polyamine fatty acid derivatives; amyl alcohol fatty acid derivatives; benzalkonium chloride; benzethonium chloride; and the like;

amphoteric surfactants including imidazoline amphoteric surfactants such as sodium 2-undecyl-N,N,N-(hydroxyethylcarboxymethyl)-2-imidazoline and 2-cocoyl-2-imidazoliniumhydroxide-1-carboxyethyloxy-2-sodium salt; betaine surfactants such as 2-heptadecyl-N-carboxymethyl-N-hydroxyethylimidazolinium betaine, lauryl dimethyl aminoacetic acid betaine, alkylbetaine, amidobetaine, and sulfobetaine; and the like; lipophilic nonionic surfactants including sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; sucrose fatty acid esters; glyceryl fatty acids such as glyceryl monocottonseed fatty acid, glyceryl monoerucate, glyceryl sesquioleate, glyceryl monostearate, glyceryl α,α'-oleate pyroglutamate, and glyceryl monostearate; polyglyceryl fatty acid esters such as diglyceryl monoisostearate and diglyceryl diisostearate; propylene glycol fatty acid esters such as propylene glycol monostearate; hydrogenated castor oil derivatives; glycerin alkyl ethers; and the like;

hydrophilic nonionic surfactants including POE sorbitan fatty acid esters such as POE sorbitan monooleate, POE sorbitan monostearate, POE sorbitan monoolate, and POE sorbitan tetraoleate; POE sorbitol fatty acid esters such as POE sorbitol monolaurate, POE sorbitol monooleate, POE sorbitol pentaoleate, and POE sorbitol monostearate; POE glycerin fatty acid esters such as POE glycerin monostearate, POE glycerin monoisostearate, and POE glycerin triisostearate; POE fatty acid esters such as POE monooleate, POE distearate, POE monodioleate, and ethylene glycol distearate; POE alkyl ethers such as POE lauryl ether, POE oleyl ether, POE stearyl ether, POE behenyl ether, POE 2-octyldodecyl ether, and POE cholestanol ether; Pluronic surfactants such as Pluronic; POE/POP alkyl ethers such as POE/POP cetyl ether, POE/POP 2-decyltetradecyl ether, POE/POP monobutyl ether, POE/POP hydrogenated lanolin, and POE/POP glycerin ether; tetra POE/tetra POP ethylenediamine polymers such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamate monoisostearate diester, and POE hydrogenated castor oil maleate; POE beeswax/lanolin derivatives such as POE sorbitol beeswax; alkanol amides such as coconut oil fatty acid diethanolamide, lauric acid monoethanolamide, and fatty acid isopropanolamide; POE propylene glycol fatty acid esters; POE alkylamines; POE fatty acid amides; sucrose fatty acid esters; POE nonylphenyl formaldehyde polymers; alkyl ethoxy dimethylamine oxides; trioleyl phosphate; and the like; natural surfactants including lecithins such as soybean phospholipid, hydrogenated soybean phospholipid, egg yolk phospholipid, and hydrogenated egg yolk phospholipid; soybean saponin; and the like;

moisturizing agents including polyethylene glycol, propylene glycol, glycerin, 1,3-butylene glycol, xylitol, sorbitol, maltitol, chondroitin sulfate, hyaluronic acid, mucoitin sulfuric acid, caronic acid, atherocollagen, cholesteryl-12-hydroxystearate, sodium lactate, urea, bile acid salts, dl-pyrrolidone carboxylates, short-chain soluble collagen, diglycerol (EO) PO adducts, *Rosa roxburghii* extracts, *Achillea millefolium* extracts, *Melilotus officinalis* extracts, and the like;

thickeners including gum Arabic, carrageenan, karaya gum, tragacanth gum, carob gum, quince seeds (marmelo), casein, dextrin, gelatin, sodium pectate, sodium alginate, methyl cellulose, ethyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite, hectorite, quaternary ammonium salt type cation-modified bentonite, quaternary ammonium salt type cation-modified hectorite, decaglycerin fatty acid ester eicosadioate condensate, and the like; preservatives including methylparaben, ethylparaben, butylparaben, and the like;

powdery components including inorganic powders such as talc, kaolin, mica, sericite, white mica, gold mica, synthetic mica, red mica, black mica, rithia mica, vermicurite, magnesium carbonate, calcium carbonate, aluminum silicate, barium silicate, calcium silicate, magnesium silicate, strontium silicate, metal salts of tungstic acid, magnesium, silica, zeolite, barium sulfate, calcined calcium sulfate (calcined gypsum), calcium phosphate, fluorine apatite, hydroxyapatite, ceramic powder, metallic soaps (zinc myristate, calcium palmitate, and aluminum stearate), and boron nitride; organic powders such as polyamide resin powder (nylon powder), polyethylene powder, methyl polymethacrylate powder, polystyrene powder, copolymer resin powder of styrene and acrylic acid, benzoguanamine resin powder, poly(ethylene tetrafluoride) powder, and cellulose powder; and the like; pigments including inorganic white pigments such as titanium dioxide and zinc oxide (including fine particles of titanium dioxide or zinc oxide which are used as an ultraviolet-scattering agent and surface-coated inorganic white pigments obtained by coating the surfaces of such fine particles with a fatty acid soap such as aluminum stearate or zinc palmitate; a fatty acid such as stearic acid, myristic acid, or palmitic acid; or a fatty acid ester such as dextrin palmitate); inorganic red pigments such as iron oxide (bengara) and iron titanate; inorganic brown pigments such as γ-iron oxide; inorganic yellow pigments such as yellow iron oxide and yellow ocher; inorganic black pigments such as black iron oxide, carbon black, and titanium suboxide; inorganic violet pigments such as mango violet and cobalt violet; inorganic green pigments such as chromium oxide, chromium hydroxide, and cobalt titanate; inorganic blue pigments such as ultramarine blue and iron blue; pearl pigments such as titanium oxide-coated mica, titanium oxide-coated bismuth oxychloride, titanium oxide-coated talc, colored titanium oxide-coated mica, bismuth oxychloride, and argentine film; metal powder pigments such as aluminum powder and copper powder; organic pigments such as Red Nos. 201, 202, 204, 205, 220, 226, 228, and 405, Orange Nos. 203 and 204, Yellow Nos. 205 and 401, and Blue No. 404; organic pigments of zirconium, barium, and aluminum lakes such as Red Nos. 3, 104, 106, 227, 230, 401, and 505, Orange No. 205, Yellow Nos. 4, 5, 202, and 203, Green No. 3, and Blue No. 1; and the like;

pH-adjusting agents including edetic acid, disodium edetate, citric acid, sodium citrate, sodium hydroxide, potassium hydroxide, triethanolamine, and the like;

antioxidants including vitamin C group, derivatives thereof, and salts thereof; tocopherols, derivatives thereof, and salts thereof; dibutyl hydroxy toluene; butyl hydroxy anisole; gallic acid ester; and the like;

ultraviolet absorbers including benzoic acid ultraviolet absorbers such as p-aminobenzoic acid (hereinafter referred to as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA octyl ester; anthranilic acid ultraviolet absorbers such as homomethyl-N-acetyl anthranilate; salicylic acid ultraviolet absorbers such as amyl salicylate, menthyl salicylate, homomethyl salicylate, octyl salicylate, phenyl salicylate, benzyl salicylate, and p-isopropanol phenyl salicylate; cinnamic acid ultraviolet absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl-p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl-mono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; urocanic acid; ethyl urocanate; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzalazine; dianisoylmethane; 4-methoxy-4'-t-butyldibenzoylmethane; 5-(3,3-dimethyl-2-norbornylidene)-3-pentan-2-one; 2,4,6-trianilino-β-(carbo-2'-ethylhexyl-1'-oxy)1,3,5-triazine; 4-tert-butyl-4'-methoxydibenzoylmethane; and the like; dyes including chlorophyll, p-carotene, and the like; perfumes including plant perfumes such as rose oil, jasmine oil, and lavender oil; synthetic perfumes such as limonene, citral, linalool, and eugenol; and the like;

sequestering agents include disodium edetate, edetic acid salts, hydroxyethane diphosphonate, and the like;

purified water; and the like.

The amount of the hair care product or the hair cosmetic product can be appropriately selected depending on the dosage form and the like. The hair care product or the hair cosmetic product can be used once to several times a day at a concentration of from 0.000001 to 3% (w/v), preferably from 0.0001 to 1% (w/v).

Advantage of the Invention

As will be described in detail in the section of Pharmacological Test below, in a European Phase III clinical trial for tafluprost, one of the 15,15-difluoroprostaglandin $F_{2\alpha}$ derivatives, with patients with open-angle glaucoma or ocular hypertension, it was found that tafluprost has actions of growing eyelashes, making eyelashes thicker, and changing the color thereof, that is, has an effect of promoting the growth of hair (eyelashes). Therefore, a 15,15-difluoroprostaglandin $F_{2\alpha}$ derivative is useful as a hair (eyelash) growth promoting agent, and it is expected that the hair growth promoting agent can be used as an active ingredient of a preventive or therapeutic agent for a disease associated with hair such as alopecia and a hair care product or a hair cosmetic product such as a hair regrowth agent, a hair growth agent, a hair density increasing agent, or a hair nourishing agent.

BEST MODE FOR CARRYING OUT THE INVENTION

Hereinafter, examples of preparations and products of the present invention and results of a pharmacological test will be described. However, these examples are described for the purpose of understanding the present invention better and are not meant to limit the scope of the present invention.
[Examples of Preparations and Products]
Hereinafter, examples of general preparations and products containing a 15,15-difluoroprostaglandin $F_{2\alpha}$ derivative according to the present invention will be described.
1. Ointment White petrolatum and lanolin are melted and filtered, and liquid petrolatum is added to the filtrate, whereby a white petrolatum mixture is prepared. On the other hand, a 15,15-difluoroprostaglandin $F_{2\alpha}$ derivative (final concentration: 2% by weight), zinc oxide and calamine are added to the rest of the liquid petrolatum, and the resulting mixture is homogenized until the mixture is finely and uniformly dispersed. This mixture is added to the previously prepared white petrolatum mixture, and the mixture is melted and stirred. Thereafter, stirring is continued until the mixture is solidified, whereby an objective ointment can be prepared.
2. Solution A 15,15-difluoroprostaglandin $F_{2\alpha}$ derivative is dissolved in water to give a final concentration of 5% by weight, and the resulting solution is sterilized by filtration, whereby an objective solution can be prepared.
3. Lotion A 15,15-difluoroprostaglandin $F_{2\alpha}$ derivative is dissolved in a vehicle containing N-methylpyrrolidone and propylene glycol, whereby an objective lotion can be prepared.
4. Aerosol A 15,15-difluoroprostaglandin $F_{2\alpha}$ derivative is dissolved in absolute alcohol to give a final concentration of 0.1% by weight, and the resulting solution is filtered to remove particles and waste threads. The filtrate is cooled to about −30° C., and a cooling mixture of dichlorofluoromethane and dichlorotetrafluoroethane is added thereto. The resulting solution is filled into a plastic-coated bottle under cooling, whereby an objective aerosol can be prepared.
[Pharmacological Test]

A European Phase III clinical trial for tafluprost, one of the 15,15-difluoroprostaglandin $F_{2\alpha}$ derivatives, with patients with open-angle glaucoma or ocular hypertension was performed by the following test method, and tafluprost was evaluated for findings associated with the eyelashes and an peripheral area thereof, that is, the evaluation was performed as to whether eyelashes were grown, eyelashes were made thicker, and the color of eyelashes was changed by the following evaluation method.

(Test Method)
Patients with open-angle glaucoma or ocular hypertension were randomly allocated to two groups (a 0.0015% tafluprost eye drop group and a 0.005% latanoprost eye drop group) and received the eye drop once a day at a dose of one drop for 24 months in a double-blind manner after a washout period for 5 days to 4 weeks or more according to need prior to the glaucoma medication.
(Evaluation Method)
The eyelashes and eyelids were photographed at 0 (base line), 3, 6, 12, 18, and 24 months, and the photographs were compared with the base line, and the presence or absence of findings (eyelashes were grown, eyelashes were made thicker, and the color of eyelashes was changed) was confirmed.
(Results)
The following Table 1 shows the number of patients for which the respective findings (eyelashes were grown, eyelashes were made thicker, and the color of eyelashes was changed) were observed when the above-mentioned test method was performed.

TABLE 1

|  | Tafluprost eye drop group (patients) | Latanoprost eye drop group (patients) |
| --- | --- | --- |
| Eyelashes were grown | 17 | 11 |
| Color of eyelashes was changed | 13 | 10 |
| Eyelashes were made thicker | 5 | 4 |

Total number of patients: 264 for both tafluprost and latanoprost groups (Discussion)
As shown in Table 1, tafluprost has actions of growing eyelashes, making eyelashes thicker, and changing the color thereof and therefore is useful as a hair growth promoting agent. These actions have significant effects as compared with those of latanoprost which is a representative $PGF_{2\alpha}$ derivative.

INDUSTRIAL APPLICABILITY

A 15,15-difluoroprostaglandin $F_{2\alpha}$ derivative is useful as a hair (eyelash) growth promoting agent, and the hair growth promoting agent can be used as an active ingredient of a preventive or therapeutic agent for a disease associated with hair such as alopecia and a hair care product or a hair cosmetic product such as a hair regrowth agent, a hair growth agent, a hair density increasing agent, or a hair nourishing agent.

The invention claimed is:

1. A method for promoting the growth of eyelashes comprising administering to an eye of a patient in need thereof a pharmacologically effective amount of tafluprost or a pharmaceutically acceptable salt thereof.

2. A method for thickening eyelashes comprising administering to an eye of a patient in need thereof a pharmacologically effective amount of tafluprost or a pharmaceutically acceptable salt thereof.

3. A method for changing the color of eyelashes comprising administering to an eye of a patient in need thereof a pharmacologically effective amount of tafluprost or a pharmaceutically acceptable salt thereof.

4. A method of treating alopecia of the eyelashes comprising administering to an eye of a patient in need thereof a pharmaceutically effective amount of tafluprost or a pharmaceutically acceptable salt thereof.

* * * * *